United States Patent [19]  
Kuekenhoener et al.

[11] Patent Number: 5,053,550
[45] Date of Patent: Oct. 1, 1991

[54] PREPARATION OF FORMYLCYCLOPROPANE

[75] Inventors: Thomas Kuekenhoener, Frankenthal; Norbert Goetz, Worms, both of Fed. Rep. of Germany

[73] Assignee: BASF Aktiengesellschaft, Ludwigshafen, Fed. Rep. of Germany

[21] Appl. No.: 533,940

[22] Filed: Jun. 4, 1990

Related U.S. Application Data

[63] Continuation of Ser. No. 342,317, Apr. 24, 1989, abandoned.

[30] Foreign Application Priority Data

May 6, 1988 [DE] Fed. Rep. of Germany ....... 3815485

[51] Int. Cl.$^5$ .............................................. C07C 45/61
[52] U.S. Cl. ..................................... 568/420; 568/488
[58] Field of Search .............................. 568/420, 488

[56] References Cited

U.S. PATENT DOCUMENTS 3,404,166 10/1968 Achard et al. ...................... 568/488
3,996,259 12/1976 Lee et al. ............................ 568/448
4,720,593 1/1988 Andrade et al. ..................... 568/420

OTHER PUBLICATIONS

Rec.Trav.Chem. 91, 221–228 (1972).
J.Org.Chem. USSR 23, 112–115 (1987).
J.Org.Chem. 52, 2559–2562 (1987).
J.Org.Chem. 50, 1332 (1985).
Bull.Soc.Chim. France, 3273 (1965).
Rozantzev:Synthesis 191 (1971).

Primary Examiner—James H. Reamer
Attorney, Agent, or Firm—John H. Shurtleff

[57] ABSTRACT

Formylcyclopropane (I)

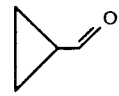

is prepared by cyclization of 4-chlorobutanal by means of an aqueous mineral base by a method in which the reaction is carried out at 50°–150° C. in a liquid two-phase system consisting of an aqueous phase and a water-immiscible organic phase, and the formylcyclopropane is removed continuously from the reaction mixture.

9 Claims, No Drawings

PREPARATION OF FORMYLCYCLOPROPANE

This application is a continuation of application Ser. No. 342,317 filed Apr. 24, 1989 now abandoned.

The present invention relates to an improved process for the preparation of formylcyclopropane (I)

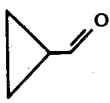

by cyclization of 4-chlorobutanal by means of an aqueous mineral base. The present invention furthermore relates to an embodiment of this process which employs a particularly advantageous method for the preparation of the starting compound 4-chlorobutanal by oxidation of 4-chlorobutanol.

Formylcyclopropane is of considerable interest as an important synthetic building block for introducing the cyclopropane group into chemical compounds, since many crop protection agents, in particular insecticides, fungicides and growth regulators, contain the cyclopropyl group.

Until recently, formylcyclopropane was obtainable only via multistage syntheses which were industrially unimportant. Its preparation from the readily obtainable and cheap 4-chlorobutanol by oxidation to 4-chlorobutanal and subsequent cyclization of the latter appeared impossible until recently since formylcyclopropane undergoes disproportionation to hydroxymethylcyclopropane and cyclopropanecarboxylic acid (Cannizzaro reaction) in the strongly basic aqueous medium of the cyclization reaction (cf. van der Maeden et al., Rec. Trav. Chim. 91 (1972), 221–228).

It was only recently that Khusid (J. Org. Chem. USSR 23 (1987), 112–115) succeeded in carrying out a simple synthesis of formylcyclopropane starting from 4-chlorobutanol. In this procedure, 4-chlorobutanol is oxidized with pyridinium chlorochromate to 4-chlorobutanal and the latter is cyclized with solid sodium hydroxide in the presence of a water-insoluble organic solvent and a phase-transfer catalyst (solid/liquid phase-transfer catalysis). The purpose of using solid/liquid phase-transfer catalysis in the cyclization reaction is to prevent the resulting formylcyclopropane from undergoing a Cannizzaro reaction, which is induced by aqueous alkali metal hydroxide solution.

This process gives good yields on the laboratory scale but is unsuitable for scaling up to the industrial scale since, on the one hand, the oxidation with pyridinium chlorochromate gives large amounts of chromium salts which entail high disposal costs and, on the other hand, the solid/liquid phase-transfer catalysis is very difficult to carry out on an industrial scale, involving expensive technical measures.

It is an object of the present invention to provide a process which can be carried out easily and is economical and which permits the preparation of formylcyclopropane from simple starting compounds on an industrial scale, if necessary continuously, while avoiding the deficiencies described.

We have found that this object is achieved by a process for the preparation of formylcyclopropane (I)

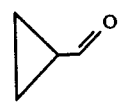

by cyclization of 4-chlorobutanal by means of an aqueous mineral base, wherein the reaction is carried out at from 50° to 150° C. in a liquid two-phase system consisting of an aqueous phase and a water-immiscible organic phase, and the formylcyclopropane is removed continuously from the reaction mixture.

We have also found an embodiment of this process, wherein the starting compound 4-chlorobutanal is prepared by oxidation of 4-chlorobutanol in a two-phase system, the oxidizing agent used being a system which consists of an aqueous sodium hypochlorite solution and a compound of the general formula II

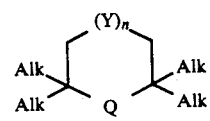

where the radicals Alk are identical or different $C_1$–$C_4$-alkyl groups, Q is one of the groups

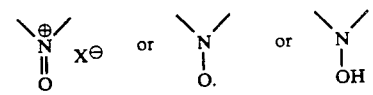

$X^\ominus$ is an anion, n is 0 or 1 and Y is oxygen, the carbonyl group or a radical

and $R^1$ and $R^2$ are each hydrogen, hydroxyl or a C-organic or O-organic radical which may furthermore be bonded to one another to form a 5-membered or 6-membered ring, and the subsequent cyclization according to the process as claimed in claim 1 is carried out without isolating the 4-chlorobutanal beforehand.

The cyclization of 4-chlorobutanal to formylcyclopropane according to equation (1).

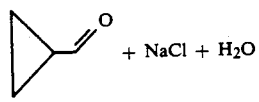

is carried out in a two-phase system consisting of an aqueous phase and an water-immiscible organic phase. The reaction can advantageously be carried out in the presence or absence of a phase-transfer catalyst. In both variants, the base used is in the aqueous phase whereas the 4-chlorobutanol is present in solution in the water-immiscible organic phase.

Suitable organic solvents for this purpose are any solvents which are inert under the reaction conditions, eg. diphenyl ether, decalin, tetralin, xylene, diphenyl and mesitylene. Solvents whose boiling point is higher than the boiling point of I or of I-containing azeotropes are preferably used.

Preferably used aqueous mineral bases are aqueous solutions of alkali metal hydroxides, in particular those of sodium hydroxide and potassium hydroxide, of alkali metal carbonates, in particular those of sodium carbonate and potassium carbonate, and of alkaline earth metal hydroxides, these basis preferably being used as from 10% strength by weight to saturated, particularly preferably from 10 to 25% by weight, solutions.

In principle any quaternary ammonium salts, eg. methyltributylammonium bromide, tetrabutylammonium chloride, methyltrioctylamnonium chloride, tetraisopentylammonium bromide, decyltributylammonium bromide, decyltripropylammonium perchlorate, cetyltributylammonium hydrogen sulfate, tetraoctylammonium benzoate, cetylpyridinium chloride, triethylbenzylammonium perfluorooctylsulfonate or tetrahexylammonium tosylate, can be used as phase-transfer catalysts, in the conventional catalytic amounts. It is also possible to use phosphonium salts, eg. tetraphenylphosphonium bromide or tetrabutylphosphonium chloride, and arsonium salts, such as tetraphenylarsonium chloride, as phase-transfer catalysts. Of course, it is also possible to employ compounds such as crown ethers, cryptands or aliphatic polyethers as such.

The cyclization can be carried out at from 50° to 150° C., particularly preferably from 90° to 130° C., in particular from 100° to 120° C. The reaction is advantageously carried out under atmospheric pressure, although it is also possible to use slightly reduced pressure.

In carrying out the process, in general the base is initially taken, if necessary together with the phase transfer catalyst and the organic solvent, the mixture is heated to the reaction temperature and the 4-chlorobutanal, or advantageously a solution of 4-chlorobutanal in a solvent which is inert under the reaction conditions, is added dropwise, and the formylcyclopropane formed is distilled off azeotropically together with water and solvent during the dropwise addition itself.

The 4-chlorobutanal can be used in pure form for the cyclization. To carry out the process on an industrial scale, however, it is particularly advantageous to prepare the 4-chlorobutanal in an upstream oxidation reaction in a two-phase system and to use the 4-chlorobutanal-containing organic phase directly, ie. without prior purification, for the cyclization. This procedure is advantageous in that the 4-chlorobutanal has high reactivity and therefore limited stability, working up the 4-chlorobutanal by distillation is dispensed with and a continuous procedure starting from 4-chlorobutanol is permitted.

In this embodiment of the process, the use of the oxidation method introduced by Anelli et al. (J. Org. Chem. 52 (1987), 255-2562) is particularly suitable for the oxidation of the 4-chlorobutanol. In this procedure, the 4-chlorobutanol is oxidized in a two-phase system, the system consisting of aqueous sodium hypochlorite solution, preferably catalytic amounts of potassium bromide and a compound of the general formula II

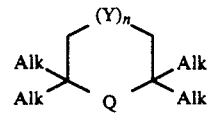

being used as the oxidizing agent. The compounds II which act as the actual oxidizing agent can be used as the commercial products or can be produced from the corresponding amines in situ, for example by reaction with hydrogen peroxide, advantageously together with sodium tungstate or similar metal oxide compounds of high oxidation state or, particularly advantageously, by reaction with peroxycarboxylic acids, in particular m-chloroperoxybenzoic acid. Specifically, the compounds II can be obtained according to Miyazawa et al. (J. Org. Chem. 50 (1985), 1332), Briere et al. (Bull. Soc. Chim. Fr. (1965), 3273) and Rozantsev et al. (Synthesis 1971, 191). 2,2,2,6-Tetramethylpiperidin-4-one (triacetoneamine) is a commercial product and is obtainable from acetone and ammonia.

In this embodiment of the process, the specific procedure adopted is one in which the compound II is initially taken in a catalytic amount dissolved in an organic solvent, 4-chlorobutanol, water and advantageously potassium bromide are then added and the pH of the aqueous phase is brought to 5–9, preferably 6.0–8.0, with the aid of a buffer, preferably a phosphate buffer. Finally, the reaction is started by slowly adding a 5–20, preferably 10–15%, strength by weight aqueous sodium hypochlorite solution at from 0° to 40° C., preferably at room temperature.

Suitable organic solvents are all those which are immiscible with water and are inert under the conditions of the oxidation reaction and of the subsequent cyclization reaction. Examples are dichloromethane, dichloroethane, tetrachloroethane, decalin, tetralin, benzene, toluene, xylene and mesitylene. The same solvent is advantageously used both in the oxidation and in the cyclization.

After the end of the oxidation, the organic phase is separated from the aqueous phase and is used, without further working up, directly for the cyclization, which is carried out in the manner described. The azeotropic distillate obtained in the course of the cyclization is freed from the water present therein and is subjected to fractional distillation to isolate the formylcyclopropane, advantageously under atmospheric or reduced pressure. In this way, formylcyclopropane is obtained in good yields.

The novel process thus permits the economical preparation of formylcyclopropane from simple starting compounds on an industrial scale and is free of the deficiencies of the previous procedures. The fact that the present process can easily be carried out by a continuous procedure, for example by effecting the two reactions in tube reactors in combination with a phase separator, is also particularly noteworthy.

The starting compound 4-chlorobutanol is a commercial product but can also easily be prepared by ether cleavage of tetrahydrofuran with hydrochloric acid (cf. Org. Synth. Coll. Vol, II (1943), 571).

EXAMPLE 1

424 g (4.0 moles) of sodium carbonate in 1.5 l of water were initially taken together with 29.6 g (0.1 mole) of tetrabutylammonium chloride and 200 ml of tetralin) and heated to 104° C. 213 g (2.0 moles) of 4-chlorobutanal, dissolved in 200 ml of tetralin, were added dropwise to the thoroughly stirred mixture at from 104° to 108° C. The formylcyclopropane was distilled off at the rate at which it was formed, from the reaction mixture, as an azeotropic mixture together with water, tetralin and a small amount of dichloromethane and tetrahydrofuran (impurities from the 4-chlorobutanal preparation). After the end of the addition of 4-chlorobutanal, distillation was continued for a further 15 minutes.

The distillate was freed from water, and the formylcyclopropane was isolated by fractional distillation (bp. 94°-97° C.). Yield: 71%.

EXAMPLE 2

35 38.8 g (0.25 mole) of triacetoneamine were dissolved in 250 ml of dichloromethane. A solution of 0.52 mole of m-chloroperoxybenzoic acid in 500 ml of dichloromethane was added dropwise and while cooling at room temperature to this solution in order to produce the nitroxyl radical, and stirring was continued for a further half hour after the addition.

A further 250 ml of dichloromethane, 1,000 ml of water, 542.5 g (5.0 moles) of 4-chlorobutanol, 29.8 g (0.25 mole) of potassium bromide and 89.0 g (0.5 mole) of disodium hydrogen phosphate dihydrate were then added to this solution at room temperature. Thereafter, the pH of the aqueous phase was brought to 6.7 by adding sodium hydroxide solution.

2,660.7 g (5.0 moles) of a 14% strength by weight aqueuous sodium hydrochlorite solution were then slowly added dropwise with through stirring, likewise at room temperature. After the addition, stirring was continued for a further 15 minutes at room temperature. The 4-chlorobutanal-containing organic phase was separated off, the aqueous phase was extracted with dichloromethane and the combined organic phases were slowly added dropwise to a mixture heated to 110° C. and consisting of a solution of 533 g of sodium hydroxide in 1,750 ml of water, 40.0 g of methyltrioctylammonium chloride and 500 ml of tetralin, the reaction mixture being stirred vigorously.

During the addition itself, an azeotropic mixture consisting of the components dichloromethane, tetrahydrofuran (formed by cyclization of unconverted 4-chloro-1butanol), water, tetralin and formylcyclopropane was distilled off. During the dropwise addition of the 4-chlorobutanal solution, an additional 750 ml of water were added to the reaction mixture in order to replace the water distilled off in the course of the azeotropic distillation. After the end of the addition and after the distillation temperature of the azeotropic mixture had reached 100° C., distillation was continued for a further 15 minutes. The resulting azeotropic distillate was freed from water and subjected to fractional distillation to isolate the formylcyclopropane. Yield (based on 4-chlorobutanol): 65%.

EXAMPLE 3

23.3 g (0.15 of triacetoneamine were dissolved in 150 ml of A solution of 0.3 mole of m-chloroperoxybenzoic acid in 450 ml of tetralin was added to this solution while cooling, and stirring was continued for a further half hour after the addition.

600 ml of water, 325.5 g (3.0 moles) of 4-chlorobutanol, 17.9 g (0.15 mole) of potassium bromide and 53.4 g (0.3 mole) of disodium hydrogen phosphate dihydrate were then added to this solution at room temperature. By adding sodium hydroxide solution, the pH of the aqueous phase was brought to 7.0.

1,650 g (3.1 moles) of a 14% strength by weight aqueous sodium hypochlorite solution were then slowly added dropwise with thorough stirring. After the addition, stirring was continued for a further 15 minutes at room temperature. The 4-chlorobutanal-containing organic phase was separated off, the aguecus phase was extracted twice with tetralin and the combined organic phases were slowly added dropwise to a mixture heated to 106° C. and consisting of 636 g 6.0 moles) of sodium carbonate, 3 l of water, 60.6 g (0.15 mole) of methyltrioctylammonium chloride and 400 ml of tetralin, the reaction mixture being stirred vigorously. During the addition itself, an azeotropic mixture consisting of the components formylcyclopropane, water, tetralin and tetrahydrofuran was distilled off. During the dropwise addition of the 4-chlorobutanal solution an additional 750 ml of water were added to the reaction mixture. After the end of the addition, distillation was continued for a further 15 minutes. The resulting distillate was freed from water and the formylcyclopropane was isolated by fractional distillation. Yield (based on 4-chlorobutanol): 56%.

EXAMPLE 4

A mixture of 213 g (2.0 moles) of 4-chlorobutanal and 200 ml of tetralin was added dropwise in the course of 90 minutes to a thoroughly stirred, boiling mixture consisting of 254 g (2.4 moles) of sodium carbonate dissolved in 1,500 ml of water and 200 ml of tetralin. During cyclopropane, unconsumed 4-chlorobutanal, water and the addition itself, an azeotropic mixture of formylcyclopropane, uncomsumed 4-chlorobutanal, water and tetralin was distilled off under atmospheric pressure.

The aqueous phase of the distillate was separated from the organic phase in a phase separator and was again extracted. Thereafter, the combined organic phases were dried over sodium sulfate and then subjected to fractional distillation. Yield: 71%.

We claim:

1. A process for the preparation of formylcyclopropane

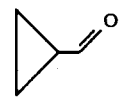

I by cyclization of 4-chlorobutanal which comprises:
reacting 4-chlorobutanal at 50°-150° C. in a liquid two-phase system consisting of an aqueous phase containing a mineral base in solution and a water-immiscible organic phase containing the 4-chlorobutanal in solution; and
continuously removing the formylcyclopropane from the reaction mixture.

2. A process as claimed in claim 1, wherein the reaction is carried out in the presence of a phase-transfer catalyst.

3. A process as claimed in claim 1, wherein the starting compound 4-chlorobutanal is prepared by oxidation or 4-chlorobutanol in a two-phase system, the oxidizing agent used being a system which consists of an aqueous sodium hypochlorite solution and a compound of the formula II

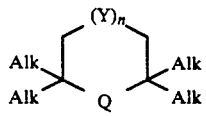 II where the radicals Alk are identical or different $C_1$-$C_4$-alkyl groups, Q is one of the groups

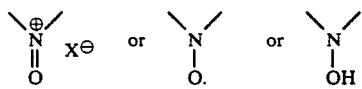

$X^\ominus$ is an anion, n is 0 or 1 and Y is oxygen, the carbonyl group or a radical

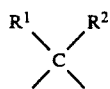

and $R^1$ and $R^2$ are each hydrogen, hydroxyl or a C-organic or O-organic radical which may furthermore be bonded to one another to form a 5-membered or 6-membered ring, and the subsequent cyclization according to the process as claimed in claim 1 is carried out without isolating the 4-chlorobutanal beforehand.

4. A process as claimed in claim 1, wherein the cyclization is carried out at from 100° to 120° C.

5. A process as claimed in claim 3, wherein the oxidation is carried out in the presence of a catalytic amount of potassium bromide.

6. A process as claimed in claim 3, which is carried out continuously in a tube reactor.

7. A process as claimed in claim 1, wherein the 4-chlorobutanol dissolved in an inert water-immiscible organic solvent is added gradually to the liquid two-phase reaction system as the formylcyclopropane is continuously removed from the reaction mixture.

8. A process as claimed in claim 1, wherein an inert water-immiscible organic solvent is used for the organic phase which has a boiling point which is higher than the boiling point of the formylcyclopropane or its azeotropes.

9. A process as claimed in claim 1, wherein the inert water-immiscible organic solvent is selected from the group consisting of benzene, toluene, dichloromethane, dichloroethane, tetrachloroethane, diphenyl ether, decalin, tetralin, xylene, diphenyl and mesitylene.

* * * * *